United States Patent [19]

Hansen et al.

[11] Patent Number: 5,356,778
[45] Date of Patent: Oct. 18, 1994

[54] METHOD FOR DETECTION OF GRAM-NEGATIVE BACTERIAL LIPOSACCHARIDES IN BIOLOGICAL FLUIDS

[75] Inventors: Eric J. Hansen, Plano; Robert S. Munford, Dallas, both of Tex.; Jussi Mertsola, Kaarina, Finland

[73] Assignee: Board of Regents, The University of Texas, Austin, Tex.

[21] Appl. No.: 972,498

[22] PCT Filed: Jul. 10, 1991

[86] PCT No.: PCT/US91/04864

§ 371 Date: Feb. 5, 1993

§ 102(e) Date: Feb. 5, 1993

[87] PCT Pub. No.: WO92/01228

PCT Pub. Date: Jan. 23, 1992

Related U.S. Application Data

[63] Continuation-in-part of Ser. No. 553,072, Jul. 13, 1990, Pat. No. 5,198,339.

[51] Int. Cl.$^5$ .................. G01N 33/579; G01N 33/53; G01N 33/569
[52] U.S. Cl. .................... 435/7.2; 435/7.32; 435/7.35; 435/7.37; 435/7.91; 435/7.92; 435/7.94; 435/810; 435/879; 435/23; 435/24; 436/71; 436/501; 436/518; 436/815; 436/821
[58] Field of Search .............. 435/7.2, 7.32, 7.35, 435/7.37, 7.91, 7.92, 7.94, 23, 24; 436/501, 518, 71, 815, 821

[56] References Cited

U.S. PATENT DOCUMENTS

| | | | |
|---|---|---|---|
| 4,455,296 | 6/1984 | Hansen et al. | 424/87 |
| 4,906,567 | 3/1990 | Connelly | 436/518 |
| 4,918,163 | 4/1990 | Young et al. | 530/387 |
| 5,198,339 | 3/1993 | Hansen et al. | 435/7.2 |

OTHER PUBLICATIONS

Mertsola, J. et al., *J. Clin. Microbiol.*, 28(12), pp. 2700-2706, Dec. 1990.

Tuffrey, M., et al., *J. Exp. Pathol.*, 71 (2), pp. 233-244, Apr. 1990, abstract only.

Bayston and Cohen, "Bacterial endotoxin and current concepts in the diagnosis and treatment of endotoxaemia", J. Med. Microbiol., vol. 31, pp. 73-83 (1990).

Article in Morbidity Mortality Weekly Report, "Increase in National Hospital Discharge Survey Rates for Septicemia-United States, 1979-87" vol. 39, No. 2, pp. 31-34 (Jan. 19, 1990).

Jacobs et al., "Septic shock in children: bacterial etiologies and temporal relationships", Pediatr. Infect. Dis. J., vol. 9, No. 3, pp. 196-200 (Mar. 1990).

Ellner, J. J., "Septic Shock", Pediatric Clinics of North America, vol. 30, No. 2 (Apr. 1983).

Cybulsky et al., "Acute Inflammatin and Microthrombosis Induced by Endotoxin, Interleukin-1, and Tumor Necrosis Factor and Their Implication in Gram-Negative Infection", Lab. Invest., v. 58, No. 4, pp. 365-378 (1988).

Levin and Bank, "The Role of Endotoxin in the Extracellular Coagulation of Limulus Blood," F. B. Bull. Johns Hopkins Hosp., vol. 115, pp. 265-274 (1964).

(List continued on next page.)

*Primary Examiner*—Toni R. Scheiner
*Attorney, Agent, or Firm*—Arnold, White & Durkee

[57] ABSTRACT

The invention relates to a method of detecting gram-negative bacterial endotoxin using antibody capture combined with amoebocyte lysate chromogenic detection. The method is highly sensitive and rapid and may be used for detection of specific endotoxin. In a particular application, picogram levels of *Haemophilus influenzae* type b endotoxin are detected in plasma taken from previously infected mammals. In another particular application, the method is applied to the detection and diagnosis of disease, through the detection of endotoxin from disease-causing organisms. A specific example is the diagnosis of chancroid through the detection of endotoxin from *H. ducreyi*.

36 Claims, 2 Drawing Sheets

OTHER PUBLICATIONS

Johgh-Leuvenink et al., "Characterization of Anti-Core Glycolipid Monoclonal Antibodies with Chemically Defined Lipopolysaccharides," Infection and Immunity, vol. 58, pp. 421-426 (Feb. 1990).

Abstract by Young et al., "Monoclonal Antibody Directed Against the 'Core' Glycolipid of Enterobacterial Endotoxin," Clinical Research vol. 30, No. 2, 522A (Apr. 1982).

Dunn et al., "Efficacy of type-specific and cross-reactive murine monoclonal antibodies directed against endotoxin during experimental sepsis," Surgery, vol. 98, No. 2, pp. 283-290 (Aug. 1985).

Salles et al., "Protective Effects of Murine Monoclonal Antibodies in Experimental Septicemia: *E. coli* Antibodies Protect Against Different Serotypes of *E. coli*," J. Infect. Dis., vol. 159, No. 4, pp. 641-647 (1989).

Erich et al., "Binding Characteristics and Cross-Reactivity of Three Different Antilipid A Monoclonal Antibodies," J. Immunol., vol. 143, No. 12, pp. 4053-4060 (Dec. 15, 1989).

Pollack et al., "Specificity and Cross-Reactivity of Monoclonal Reactive with the Core and Lipid A Regions of Bacterial Lipopolysaccharide," J. of Infect. Dis., vol. 159, No. 2, pp. 168-188 (Feb. 1989).

Teng et al., "Protection against gram-negative bacteremia and endotoxemia with human monoclonal IgM antibodies," Proc. Natl. Acad. Sci. U.S.A., vol. 82, pp. 1790-1794 (Mar. 1985).

Kirkland et al., "Analysis of the fine specificity and Cross-Reactivity of monoclonal anti-lipid A antibodies," J. Immunol., vol. 137, No. 11, pp. 3614-3619 (Dec. 1986).

Gulig et al., "Conservation of Epitopes in the Oligosaccharide Portion of the Lipoligosaccharide of *Haemophilus influenzae* Type b," Infect. and Immun., vol. 55, No. 3, pp. 513-520 (Mar. 1987).

Hansen et al., "Identification of Immunogenic Outer Membrane Proteins of *Haemophilus influenzae* Type b in the Infant Rat Model System," Infect. and Immun., vol. 32, No. 3, pp. 1084-1092 (Jun. 1981).

Kimura et al., "*Haemophilus influenzae* Type b Lipooligosaccharide: Stability of Expression and Association with Virulence," Infect. and Immunity, vol. 55, No. 9, pp. 1979-1986 (Sep. 1987).

Mutharia et al., "Monoclonal Antibodies Specific for *Escherichia coli* J5 Lipopolysaccharide: Cross-Reaction with Other Gram-Negative Bacterial Species," Infect. and Immun., vol. 45, No. 3, pp. 631-636 (Sep. 1984).

Ziegler et al., "Treatment of Gram-Negative Bacteremia and Shock with Human Antiserum To a Mutant *Escherichia coli*," New England J. of Med., vol. 307, No. 20 (Nov. 1982).

Kirkland et al., "An Immunoprotective Monoclonal Antibody to Lipopolysaccharide," J. of Immun., vol. 132, No. 5, pp. 2590-2592 (May 1984).

Aydintug et al., "Cross-Reactivity of Monoclonal Antibodies to *Escherichia coli* J5 with Herterologous Gram-Negative Bacteria and Extracted Lipopolysaccharides," J. of Infect. Dis., vol. 160, No. 5, pp. 846-857 (Nov. 1989).

Bogard et al., "Isolation and Characterization of Murine Monoclonal Antibodies Specific for Gram-Negative Bacterial Lipopolysaccharide: Association of Cross-Genus Reactivity with Lipid A Specificity," Infect. and Immun., vol. 55, No. 4, pp. 899-908 (Apr. 1987).

Mertsola et al., "Specific detection of *Haemophilus influenzae* type b lipooligosaccharide by a polymyxin B monoclonal antibody assay," J. of Immunological Methods, vol. 122, pp. 219-226 (1989).

Parent et al., "Reactivity of Monoclonal Antibody E5 ® with Endotoxin. II. Binding to Short- and Long-Chain Smooth Lipopolysaccharides," *Circulatory Shock*, 38:63-73, 1992.

Mertsola, J., Ramilo, O., Sáez-LLorens, X., Mustafa, G. H., McCracken, Jr., and Hansen, E. J., "Specific Detection of *Haemophilus influenzae* Type b Lipooligosaccharide (Hib-LOS) by Immunoassays", Interscience Conference for Antimicrobial Agents and Chemotherapy, Aug., 1989.

METHOD FOR DETECTION OF GRAM-NEGATIVE BACTERIAL LIPOSACCHARIDES IN BIOLOGICAL FLUIDS

The United States Government may have certain rights in the present invention pursuant to the terms of Grant No. HD22766 awarded by the National Institutes of Health.

This application is a continuation-in-part of U.S. Ser. No. 553,072, filed Jul. 13, 1990 which issued as U.S. Pat. No. 5,198,339.

FIELD OF THE INVENTION

The present invention relates to a method for the detection of bacterial endotoxin in a biological fluid or in a fluid intended for clinical or pharmaceutical use, using antibodies cross-reactive with a broad range of gram-negative bacteria to act as lipopolysaccharide capture agents. In particular, the method provides a sensitive assay that can be tailored to detect the endotoxin of selected gram-negative bacteria.

| LIST OF ABBREVIATIONS | |
|---|---|
| *Haemophilus influenzae* type b | Hib |
| lipooligosaccharide | LOS |
| polymyxin B | PMB |
| immunolimulus | IML |
| chromogenic *Limulus amoebocyte* assay | CLAL |
| *Limulus amoebocyte* lysate | LAL |
| lipopolysaccharide | LPS |
| monoclonal antibodies | MAbs |
| enzyme-linked immunosorbent assay | ELISA |
| outer membrane vesicles | OMV |
| sodium dodecyl sulfate | SDS |
| polyacrylamide gel electrophoresis | PAGE |
| pyrogen-free | pf |
| immunoglobulin G | IgG |
| phosphate buffered saline | PBS |
| Tween 20 | Tw |
| bovine serum albumin | BSA |
| cerebrospinal fluid | CSF |
| colony forming units | CFU |
| brain heart infusion broth supplemented with Levinthal base | BHIs |

DESCRIPTION OF THE RELATED ART

Septicemia is a potentially fatal clinical condition which is currently increasing in importance, possibly because of the longer survival of immunocompromised patients and greater use of invasive techniques in medicine (1,2). It has been estimated that the incidence of this disease has increased ten-fold during the last 20 years and that the number of cases annually is from 100,000 to 300,000 in the United States alone (3). From 20% to 40% of the patients with gram-negative bacterial septicemia have shock and, of these, approximately 75% will die (1). In children, *Haemophilus influenzae* type b (Hib) is responsible for about 40% of cases of septic shock (4). *Pseudomonas aeruginosa* bacteremia in neutropenic patients is a particularly virulent form of septicemia.

Specific laboratory diagnosis of gram-negative septicemia is usually performed by culturing blood samples. These methods, however, are relatively slow, requiring several hours to days to detect bacterial growth.

Endotoxin is considered to be a key element in the initiation of the inflammatory cascade during gram-negative bacterial infections (5). Therefore, quantitation of these molecules in blood samples of septic patients has been considered to be important. An easy and relatively sensitive way to detect endotoxin involves the Limulus amoebocyte lysate (LAL) assay (6). The LAL assay, however, has several problems which have limited its usefulness in the diagnosis of septicemia. This assay is sensitive to trace amounts of LPS contamination in laboratory fluids and reagents, which then cause false-positive reactions. Furthermore, plasma of patients has several nonspecific activators and inhibitors of the enzymes involved in the LAL reaction. Finally, the color and turbidity of normal plasma impedes the high sensitivity of a recent refinement of the LAL method known as the CLAL assay. The latter method measures color generated by the action of activated lysate enzymes on a synthetic chromogenic substrate. Because of these problems, the sensitivity and specificity of the LAL and CLAL assays are thought to be suboptimal for reliable clinical diagnosis.

The basic structure of lipopolysaccharide (LPS) involves three relatively well defined regions and is similar in all gram-negative bacteria. These regions are an O-specific side chain, the core oligosaccharide, and lipid A. The O-specific region is composed of repeating oligosaccharide units each having 2–6 saccharides. The core lies between the O-specific side chains and lipid A and is a branching oligosaccharide having representative sugars such as glucose, N-acetylglucosamine and galactose. In the core region proximal to Lipid A, heptose and keto-deoxyoctonate are commonly found. There is considerable structural variation among the gram-negative bacteria in the O-chain region, but only minor variation throughout the core region with structure being highly conserved in the inner core region proximal to Lipid A. The most highly conserved portion of the LPS molecule is lipid A, a phosphorylated glucosamine disaccharide, to which long chain fatty acids are attached.

Some gram-negative bacteria, including *Haemophilus influenzae, Neisseria meningitidis, N. gonorrhoeae* and *Bordetella pertussis*, synthesize a different type of LPS molecule that has been designated as lipooligosaccharide (LOS). LOS is very similar to the LPS molecule except that LOS does not have an O-antigen but consists of lipid A and core oligosaccharide. LOS is, like LPS, an endotoxin.

The general structure of a typical gram-negative lipopolysaccharide, *S. typhimurium*, is shown in FIG. 1.

Realization that the core region of bacterial lipopolysaccharide is highly conserved has resulted in a search for antibodies that will cross react with the endotoxin of all gram-negative species. Some claimed highly cross reactive monoclonal antibodies have been obtained, for example, several of which are directed toward Lipid A (7-9). Monoclonal antibodies binding specifically with *Escherichia coli* strains have been produced by immunization of mice with bacterial mutants lacking the O-side chain and part of the core polysaccharide (10). At least some of the reported monoclonal antibodies have cross reactivity in detecting LPS despite the fact that in many instances cross reactivity has not been convincingly demonstrated (1). Theoretically, antibodies to the LPS core of any one or at most a few gram-negative bacteria should interact with all gram-negative bacteria having the general core structure of LPS shown in FIG. 1.

XMMEN-OE5 produces a monoclonal antibody that binds epitopes on LPS associated with the endotoxin core glycolipid of gram-negative bacteria (11). The disclosed antibodies have broad cross reactivity with gram-negative bacteria of different genera and effectively neutralize endotoxin. Potential assays using these monoclonal antibodies have been suggested, including quantification of endotoxin using standard ELISA techniques well known to those skilled in the art. However, standard methods in immunodiagnosis lack the high sensitivity of the Limulus assay.

The ability of the amoebocyte lysate used in the CLAL assay to react with gram-negative endotoxin has been used to develop an assay for detecting lipopolysaccharides. Endotoxin is bound to a capture agent prepared from an amoebocyte lysate (12). The bound endotoxin is then detected, for example, by antigenic analysis. The limit of detection for *Escherichia coli* K235 LPS by this method was 10 ng. The method of this patent is said to be selective for gram-negative endotoxin, but it is far less sensitive than the CLAL assay which can detect picogram quantities. The general utility of the claimed method is therefore limited due to its lack of sensitivity, especially in clinical applications where it is important to detect even very small amounts of LPS or very small numbers of bacteria. Furthermore, very low limits of detection are critical in analysis of sterile solutions for in vivo use.

Thus, there is a need for a general method of detection of bacterial endotoxin which is rapid, specific and sensitive at least to picogram quantities. A versatile assay in principle capable of detecting several different gram-negative pathogens would be particularly useful in clinical situations where the identity of the microorganism as a gram-negative bacterium would determine the specific course of treatment.

The present invention relates generally to a sensitive and selective method for the detection of bacterial endotoxins. The method combines the use of monoclonal or polyclonal antibodies as capture agents and the known sensitivity of the chromogenic Limulus amoebocyte lysate detection system.

Generally, detection of bacterial endotoxin in accordance with the invention includes the steps of contacting a sample suspected of containing a bacterial endotoxin with at least one antibody capable of binding such bacterial endotoxin, wherein the sample is contacted with the antibody under conditions effective to bind the antibody to endotoxin that may be present in the sample. Then, the antibody-bound endotoxin is washed to remove contaminants, and the endotoxin then detected through the application of an amoebocyte lysate.

In more particular embodiments, the method is performed by attaching antibodies of the desired specificity to a solid surface, incubating the surface with a sample suspected of containing endotoxin, washing the matrix-bound endotoxin, adding and incubating the bound endotoxin with Limulus amoebocyte lysate and finally adding a substrate of the lysate to form a product that can be detected. In preferred embodiments, the amount of endotoxin may be measured, in that the amount of product will generally be proportional to the amount of bound endotoxin.

Attachment of antibodies to a solid surface is commonly used for immobilization and is most often achieved by simply coating a hard surface with the antibodies. The antibodies can be attached to any solid surface to which they will adhere. In usual practice, antibodies are adsorbed to the plastic surface of microtiter plate wells, but adsorption could be to any suitable surface. It is important to block uncoated sites to prevent nonspecific binding of interfering substances from the sample. This is normally done with proteins, for example, albumin, but other surface blocking agents that do not interfere with the assay could be used.

Excess blocking agents are washed from the surface after reacting with nonspecific binding sites. The wash solution is usually pyrogen-free phosphate buffered saline (pf-PBS) containing Tween 20. It is likely that the presence of detergent increases washing effectiveness. It should be noted that where amoebocyte lysate was used as the capture agent, washing the surface with surfactants such as polyoxyethylene sorbitan monolaurate or deoxycholate caused high levels of nonspecific binding to the immobilized lysate (12); however, that system differs from that of the present invention in that the immobilized lysate is used for capture, not detection. It is possible that detergents may affect antibody capture binding, but in view of the high sensitivity of the method, detrimental effects appear unlikely.

The inventors have found that the nature of the antibody (e.g., the degree of cross-reactivity, binding affinity, etc.) determines the broadness or narrowness of detection of specific endotoxins. Although any cross-reactive antibodies can be used as capture agents for bacterial endotoxin, it is preferable to use a limited number of monoclonal antibodies directed toward the highly conserved region of endotoxin core glycolipid in detecting lipopolysaccharide (LPS) and lipooligosaccharide (LOS) found in a wide range of gram-negative bacteria. This includes intact bacteria as well as vesicles or blebs shed or exposed on bacteria and to which the capture antibodies can bind. Examples, not intended to be limiting, of endotoxin from bacteria which could be detected include Escherichia, Bordetella, Branhamella, Salmonella, Haemophilus, Klebsiella, Proteus, Enterobacter, Pseudomonas, Pasteurella, Acinetobacter, Chlamydia and Neisseria and in general any bacteria whose LPS is capable of binding to the selected antibodies.

The practitioner will appreciate that the purpose of the antibodies is to act as capture agents in selectively binding endotoxin, a toxic component of the gram-negative bacterial membrane. There are thus several choices of antibodies. For example, a surface could be coated with antibodies directed specifically to the core oligosaccharide distal to lipid A in any species of gram-negative bacteria. Capture specificity would be then directed toward one or a limited group of bacteria, depending on cross reactivity. On the other hand, antibodies directed toward epitopes proximal to lipid A or to lipid A itself would be expected to display broad cross reactivity toward virtually all classes of gram-negative bacteria.

Selection of the monoclonal antibodies to be used as capture agents is an aspect of this invention that shows its versatility. For example, to detect a range of bacterial endotoxin from several species, one could select antibodies to lipid A or the lipid A/KDO region of LPS since this core region is highly conserved among gram-negative bacteria. Some experimentation may be necessary to obtain an optimal panel of MAb, but there are several references with detailed procedures for producing antibodies of good cross reactivity (7,13,14,16). At least two clones found to secrete monoclonal antibody stably are available as hybridomas XMMEN-OE5 and XMMEN-LY1 and are on deposit with the American Type Culture Collection with respective ATCC Accession Nos. HB9081 and HB9082 (11). The hybridomas have been deposited with the American Type Culture Collection, 12301 Parklawn Drive, Rocklawn, Md. 20852 USA. Deposit has been accepted under the Budapest Treaty on the International Recognition of the Deposit of Microorganisms for the purpose of Patent Procedure. All restrictions on the availability to the public of the material will irrevocably removed upon the granting of a patent. The monoclonal antibodies produced by these cell lines show broad cross reactivity against gram-negative bacteria and could be used as capture agents for detecting bacterial endotoxin.

Antibodies could also be developed using experimental techniques known to those skilled in the art. In particular, suitable antibodies may be selected from hybridomas obtained from immunizations and hybridoma fusions involving several species of rough mutants of gram-negative bacteria. Rough mutants can be selected from wild-type colonies on the basis of their appearance which contrasts with the smooth appearance of wild-type colonies. The rough appearance is the result of deletion of O-antigen. As a result of the deletions, portions of the core become more exposed, enabling formation of a wider selection of antibodies directed to epitopes in the exposed regions. Most preferred monoclonal antibodies would be specific for lipid A or perhaps alternatively for a smaller fragment of lipid A.

To assure detection of a wide range of bacterial endotoxin, a panel of 3-4 monoclonal antibodies would be selected, preferably those directed toward heptose/KDO regions of the core. This region is adjacent to lipid A and comprises several unusual 2-keto sugars, particularly 3-deoxy-D-manno-octulosonic acid (KDO). Selected antibodies could include MAbs 4-7B5 (7), 8A1 (9), 7G (16), A6(H4C5) (15), 8-2C1 (7), or HA-1A (21). The broadly cross-reactive monoclonal antibody produced by hybridoma cell line XMMEN-OE5 (ATCC Accession No. HB9081) would also serve as a capture agent, either in combination with the other antibodies or, depending on the degree of cross reactivity required, by itself (11).

The sample in which bacterial LOS or LPS is to be detected is usually a body fluid such as plasma, serum, cerebrospinal fluid, urine, saliva, urethral secretions, sputum or the like, all being fluids that either are normally sterile or do not contain the organism of interest. The method is, however, of general application and could be used to detect endotoxin contamination in sterile preparations, and in fluids intended for clinical or pharmaceutical use, or use in food products.

Samples to be tested for endotoxin may need to be diluted, usually with pyrogen-free diluent, preferably phosphate-buffered saline. Dilution would depend on the type of sample and on the amount of endotoxin present. In any event, prior to incubation with the immobilized capture antibody, the sample for testing is subjected to heat treatment, preferably at 75° C. for about 12 min, in order to inactivate materials that would later interfere with the Limulus chromogenic assay. Heating may also facilitate exposure of binding sites to the capture agent.

Once the sample is prepared for analysis, it is then incubated with the capture antibody or antibodies. When microtiter plate wells are used, this is simply a matter of adding a measured amount of sample to the wells and incubating for a time sufficient for binding to occur, usually about an hour incubation at 37° C. Other incubation times may be employed as required depending on the species of endotoxin detected. Incubation could also be performed at room temperature, although longer times to effect binding may be necessary.

Where desired, measurement of endotoxin is accomplished by adding an agent capable of detecting the protease, whose release is stimulated by the presence of endotoxin. Amoebocyte lysate contains factors that, in the presence of endotoxin, initiate a cascade that releases, among others, serine proteases. A most preferred source of lysate is the blood of *Limulus polyphemus*, but other organisms may be used, for example *Tachypleus tridentatus*. Adding a protease substrate, usually a chromogenic compound, to the lysate sample containing endotoxin allows cleavage of the substrate and release of a chromophore which can be detected spectrophotometrically. The amount of protease activated is proportional to the amount of endotoxin bound by the capture monoclonal antibody and thus the rate of color formation will be proportional to the amount of endotoxin present in the sample.

In a preferred embodiment, the chromogenic substrate is N-benzoyl-val-arg-p-nitroanilide in which release of the C-terminal chromogenic moiety is measured at 410 nm. Other chromogens could be used, for example tetramethylbenzidine, or different p-nitroanilide substrates. Quantitation could also be effected using other labels and other detection means, including fluorescent and isotopic labels or initiation of secondary reactions so long as the reaction is proportional to the protease activated by the endotoxin. A standard curve can be generated using a purified endotoxin or, preferably, the U.S. standard endotoxin as the standard.

In a particular example of the invention, the specific detection of *Haemophilus influenzae* type b endotoxin in biological fluids is demonstrated. The capture monoclonal antibody is bound to a matrix, typically plastic microtiter wells, which preferably is then blocked with a protein, usually bovine serum albumin, fetal calf serum, etc. Any Hib LOS endotoxin present in the sample will be bound to the capture antibody and not to unexposed surface. In a preferred embodiment, the capture agent comprises two monoclonal antibodies, one directed against an epitope in the oligosaccharide region of a first endotoxin and the other directed against an epitope in the oligosaccharide region of a second endotoxin. In the detection of Hib endotoxin, a preferred embodiment employs a first antibody that recognizes endotoxin from a first strain, such as Hib LOS DL26, and a second antibody that recognizes endotoxin from a second strain, such as Hib LOS DL42. Preferred examples include monoclonal antibodies 12D9 and 4C4, respectively (ATCC accession numbers HB10462 and HB10461, respectively). Both are IgG3 type immunoglobulins. A single capture agent could be used but not all strains of *Haemophilus influenza* type b would be detected.

After contacting the test sample with the matrix bound monoclonal antibody, bound LOS is washed to remove nonbinding substances present, preferably with pf-PBS containing a detergent such as Tween 20. In a subsequent step, the surface-bound LOS is incubated with an amoebocyte lysate, preferably Limulus amoebocyte lysate. The incubation is usually performed at 37°, allowing activation of a protease system from the lysate by bound endotoxin. In a final step, a chromogenic substrate is added and the optical density of the sample is read after standing at room temperature, preferably for 30 minutes. Optical density may be read on a spectrophotometer, such as the ELISA reader. Standards may be included with the test sample and from them concentrations of endotoxin in the samples determined.

It has further been demonstrated that the present invention may be applied to provide a rapid, definitive diagnosis of chancroid, the causative agent of which is *Haemophilus ducreyi*. Through the use of a monoclonal antibody specific for LOS of *H. ducreyi* in the special Limulus amoebocyte lysate assay of the present invention, as few as 50 cfu of *H. duceryi* grown in vitro and resuspended in saline could be detected. Moreover, as few as 500 cfu in aspirated material from a rabbit model of chancroid could be detected.

The method of the present invention is simple and rapid. Tests can generally be completed within three hours after sample preparation. Typically, the sample is incubated with the capture antibody for an hour at 37° C., washed, incubated about 20 min at room temperature with amoebocyte lysate and further incubated at room temperature after addition of chromogenic substrate. Thus, measurements may be made within three hours of incubating the sample in microtiter wells coated with capture antibody.

The inventors have demonstrated the specificity of the invention with Hib LOS detection; however, it will be appreciated that other pathogens of clinical importance may be readily detected using appropriate antibodies. For example, the method is readily adapted to specific detection of *Pseudomonas aeruginosa* and *Pseudomonas maltophilia* by employing the monoclonal antibody XMMPS-605 produced by the hybridoma cell line having ATCC Accession No. HB8909 (11). The development of other specific diagnoses is limited only by the availability of the capture antibody or antibodies required and not by the general applicability of the method.

It is contemplated that one or more kits will be useful for the practice of the method of the present invention. Such kits would contain separate containers comprising monoclonal antibodies suitable for the detection of all or a limited selection of bacterial endotoxins. In addition, containers comprising an amoebocyte lysate and a chromogenic substrate to detect release of lysate protease would be provided, all preferably in lyophilized form. In one particular kit for detection of bacterial endotoxin, the monoclonal antibody from hybridoma cell line XMMEN-OE5 alone or in combination with one or more of the monoclonal antibodies 4-7B5, 8A1, A6 and 8-2C1 would be provided. For the detection of *Haemophilus influenzae* type b MAb 4C4 and MAb 12D9 would be provided.

FIG. 1 shows the structure of *S. typhimurium* lipopolysaccharide which is similar to the lipopolysaccharide of other gram-negative bacteria. $R_a$, $R_b$, $R_c$, $R_{d1}$ and $R_e$ designate the structures of LPS molecules synthesized by different mutants of Samonella.

FIG. 2 indicates the detection of Hib DL42 LOS in PBS ( ) and in plasma-PBS (diluted 1:3) ( ) and Hib DL42 bacteria in plasma-PBS (diluted 1:3) ( ) by immunolimulus assay. Open symbols indicate nonspecific background. Results are means from duplicate wells.

Figure 1:
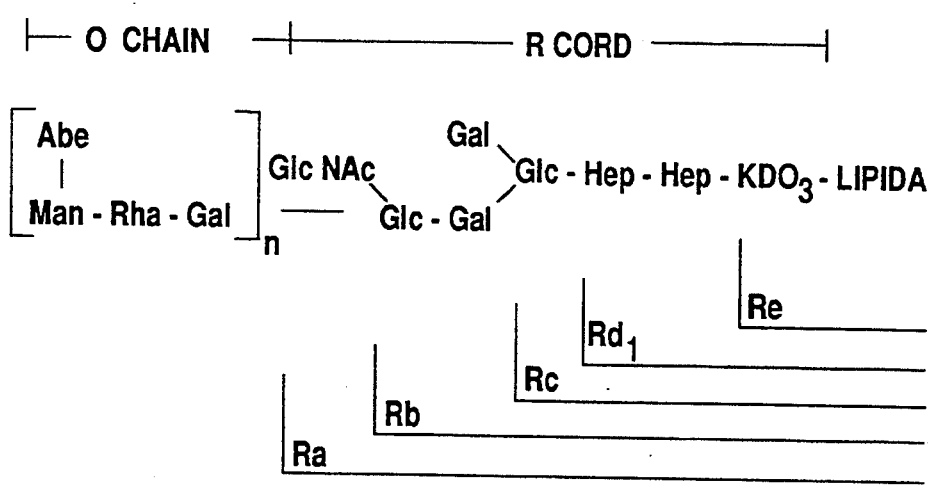

As discussed above, the invention is a sensitive and rapid assay that can be designed to detect gram-negative bacterial endotoxin, or, modified to detect specific species of bacterial endotoxin. In particular, the method is useful for detection of very low levels of endotoxin.

The inventors have used antibodies as the basis of selectivity of their method and combined the previously known reaction with amoebocyte lysate to provide an assay that is highly sensitive. The antibodies are preferably monoclonal antibodies directed to designated regions of the endotoxin core of LPS/LOS. As an example of how the method is practiced, the following details refer particularly to the detection of *Haemophilus influenzae* type b endotoxin (Hib LOS); however, analogous considerations apply to detection of other species with different-antibodies, one or more, being used. An inclusive method to detect gram-negative bacterial endotoxins, for example, would require up to several monoclonal antibodies directed to regions at or very close to the endotoxin lipid A core. A method to detect *Pseudomonas aeruginosa* could employ monoclonal antibody XMMPS-605 (ATCC Accession No. HB8909 (11)).

Materials and Methods

Bacterial Strains and Culture Conditions

Hib strain DL42 has been characterized extensively (17). Another Hib strain (DL301) used in this study was a recent isolate from a child with Hib meningitis in Dallas. Both of these strains belong to Hib LOS antigenic group 2, as determined by their reactivity with MAb 4C4 in the colony blot-radioimmunoassay stem (17). Encapsulated *Escherichia coli* K1 (77-436) and Hib strain DL26, from Hib LOS antigenic group 1 (17) were used for control experiments. These strains do not react with MAb 4C4.

Hib strains were grown in brain-heart infusion medium (Difco Laboratories, Detroit, MI) supplemented with Levinthal's base (BHIs) as previously described (18). *Escherichia coli* K1 was grown in brain-heart infusion medium without the supplement.

Endotoxins

LOS from Hib strain DL42 was purified by means of the modified hot phenol-water method (19). Purified LOS was diluted in pyrogen-free saline (Abbott Laboratories, North Chicago, Ill.) and stored in 1 $\mu$g/ml concentrations at $-70°$ C. until used as a standard in the assays. LPS purified from *Escherichia coli* O111:B4 (Sigma No. L-33012) was purchased from Sigma Chemical Company, St. Louis, Mo., as were LPS from *Escherichia coli* O127:B8 (Sigma No. L-3137), Klebsiella pneumoniae (Sigma No. L-1770) and *Pseudomonas aeruginosa* (Sigma No. L-8643).

Monoclonal Antibodies (MAbs)

MAb 4C4 (ATCC Accession No. HB10461), directed against an epitope in the oligosaccharide portion of the LOS molecules of Hib strains belonging to Hib LOS antigenic group 2, has been described previously. This MAb reacts with the LOS from Hib strains DL42 and DL301 and, additionally, was able to recognize 86% of the Hib clinical isolates recently tested (17).

Other Materials

Sterile polystyrene ELISA plates were purchased from Corning Laboratory Sciences, Houston, Tex. All plates were determined to be pyrogen-free prior to use. Each vial of LAL (Pyrotell, Associates of Cape Code, Woods Hole, Mass. specified to be suitable for use in the CLAL) was reconstituted with 10 ml of pf-water and stored in multiple portions at −20° C. for less than 3 months. For the IML assay, the LAL was diluted with 20 ml of pf-water. N-benzoyl-val-gly-arg-p-nitroanilide hydrochloride (Sigma No. B-4758) was diluted to a concentration of 0.7 mg/ml in pf-water and stored at 4° C. until used in the assays.

Statistical Analysis

Pearson's correlation coefficient was used to assess the strength of the relationship between the results from the CLAL and IML assays and the magnitude of bacteremia in the animals.

The following examples are intended by way of illustration of specific embodiments of the present invention and are not intended to be limiting to the extent of describing all possible embodiments. Those skilled in the field will recognize that modification could made to the disclosed methods and applications that would remain within the scope of the present invention.

EXAMPLE 1

Immunolimulus Assay for Hib LOS Using Purified Hib LOS and Bacteria

Microtiter plates were coated overnight at room temperature with purified MAb 4C4 diluted 1:500 in 0.1M sodium carbonate buffer, pH 9.6 (20). The final amount of antibody incubated in the well was 800 ng. The microtiter wells were washed three times with pf-PBS containing 0.05% (v/v) Tween 20 (pf PBS-Tw) and then blocked with 1% (vol/vol) fetal calf serum (20) in carbonate buffer for one hour at 37° C. The plates were again washed three times with pf-PBS-Tw. Plasma for dilution of purified LOS samples was obtained by collecting blood by cardiac puncture from 50 normal infant rats, centrifuging and pooling the plasma derived by the sodium citrate method. Plasma aliquots were stored at −70° C. and prior to use as diluent were diluted 1:3 in pyrogen-free phosphate buffered saline (pf-PBS, pH 7.4).

Purified Hib DL42 LOS was diluted in pf-PBS and in plasma:PBS (diluted 1:3) and Hib bacteria were diluted in plasma:PBS (diluted 1:3). Purified Hib LOS standards were prepared in 0–1,000 pg/ml concentrations in the appropriate dilution fluid. After heat-inactivation at 75° C. for 12 min, 50 μl of the test samples and the standards were incubated in the microtiter wells, for one hour at 37° C. The wells were washed six times with pf-PBS-Tw and then filled with 50 μl LAL extract in pf-water. After 20 minutes incubation at room temperature, 50 μl of the chromogenic substrate was added and the plates were incubated 30 minutes at room temperature. The optical density was then measured using the ELISA reader and the concentrations of LOS in the test samples were obtained from the standards included on each plate.

Figure 2:
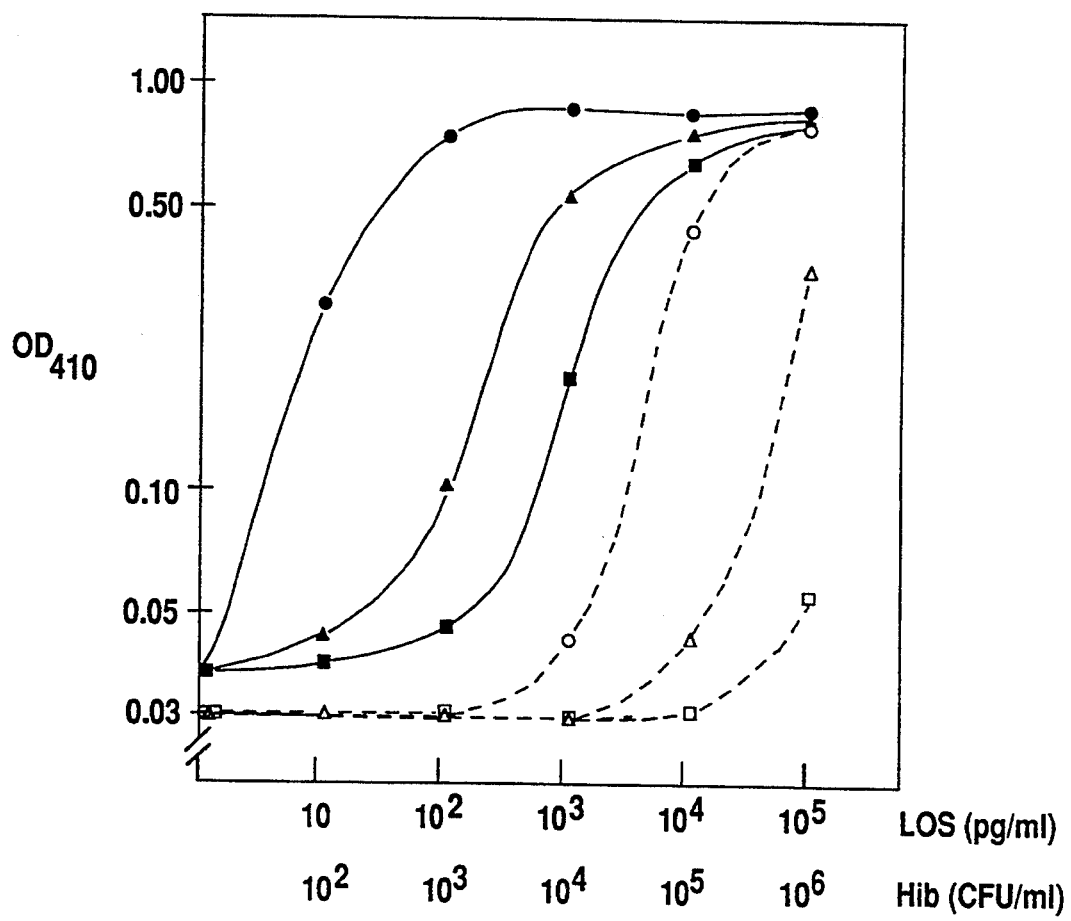

The limit of sensitivity (the concentration of LOS yielding an optical density reading exceeding the mean +2SD of the background) was 2 pg/ml in pf-PBS and 10 pg/ml in diluted plasma (FIG. 2). The sensitivity of the IML method in detecting LOS in diluted plasma containing various numbers of Hib organisms corresponded to a concentration of 300 CFU/ml, respectively.

The specificity of the IML assay is based on its ability to detect only those LOS molecules bound to the solid phase by the MAbs. As shown in FIG. 2, the nonspecific background (obtained with wells without MAb) remained consistently low during testing of plasma samples when the concentration of LOS was less than 1,000 pg/ml or when the concentration of bacteria was less than $10^5$ CFU/ml. With higher concentrations of either LOS or Hib the background increased and the IML assay lost its antibody-dependent specificity although it showed the presence of endotoxin with the CLAL-type reaction. The specific antibody binding could be demonstrated in these cases with the further dilution of the test samples.

EXAMPLE 2

Immunolimulus Assay for Purified Hib LOS in Plasma

Purified Hib DL42 LOS and purified LPS samples from four different gram-negative enteric bacteria were added in varying concentrations to normal infant rat plasma, diluted 1:3 in PBS, then heated at 75° C. for 12 min. The samples were tested with the immunolimulus assay as detailed in Example 1. Results are shown in Table 1 and indicate a high degree of specificity for the IML assay system. At LPS concentrations of less than or equal to 10 ng/ml, the optical density results were at background level; at higher concentrations, the results showed only non-specific reactions.

TABLE 1

Detection of Hib LOS by immunolimulus assay in normal infant rat plasma samples containing different concentrations of LOS/LPS.

| Strain | | Concentration of LOS/LPS in Plasma | | |
|---|---|---|---|---|
| | | 100 ng/ml | 10 ng/ml | 1 ng/ml |
| Hib DL42 | A[a] | 0.873[d] | 0.708 | 0.515 |
| | B[b] | 0.412 | 0.073 | 0.030 |
| | C[c] | 0.461 | 0.635 | 0.485 |
| E. coli O:111 | A | 0.278 | 0.027 | 0.027 |
| | B | 0.322 | 0.031 | 0.028 |
| | C | 0 | 0 | 0 |
| E. coli O:127 | A | 0.333 | 0.029 | 0.027 |
| | B | 0.409 | 0.030 | 0.026 |
| | C | 0 | 0 | 0.001 |
| K. pneumoniae | A | 0.044 | 0.027 | 0.027 |
| | B | 0.043 | 0.028 | 0.026 |
| | C | 0.001 | 0 | 0.001 |
| P. aeruginosa | A | 0.106 | 0.029 | 0.029 |
| | B | 0.147 | 0.030 | 0.028 |
| | C | 0 | 0 | 0.001 |

[a]Optical density obtained from wells coated with MAb 4C4
[b]Optical density obtained from wells lacking MAb 4C4 (control for nonspecific binding)
[c]Difference between wells A and B
[d]Results are means from duplicate wells

EXAMPLE 3

Immunolimulus Assay for Hib LOS in Plasma from Rats Infected with Hib

Five-day old infant rats were infected intranasally with $1-3 \times 10^8$ colony forming units (CFU) of Hib as described (19). For control experiments with *Escherichia coli* K1, the rats were infected by intraperitoneal inoculation with 100 or 1,000 CFU in 0.1 ml PBS. Blood cultures were obtained by taking 10 μl of blood from the tail vein at various time points (15–48 hours) after bacterial challenge. The magnitude of bacteremia was determined by spreading blood samples on BHIs-agar plates. Immediately after the blood sampling from the tail vein, cardiac puncture was performed on the same animals anesthetized with ether and blood was collected in syringes containing 3.8% (wt/vol) sodium citrate (0.05 ml of sodium citrate/0.5 ml of blood). Blood was centrifuged at 5,000 rpm in an Eppendorf centrifuge for 10 minutes at room temperature and plasma was transferred to polypropylene screw-cap tubes and stored at −70° C.

Figure 3:
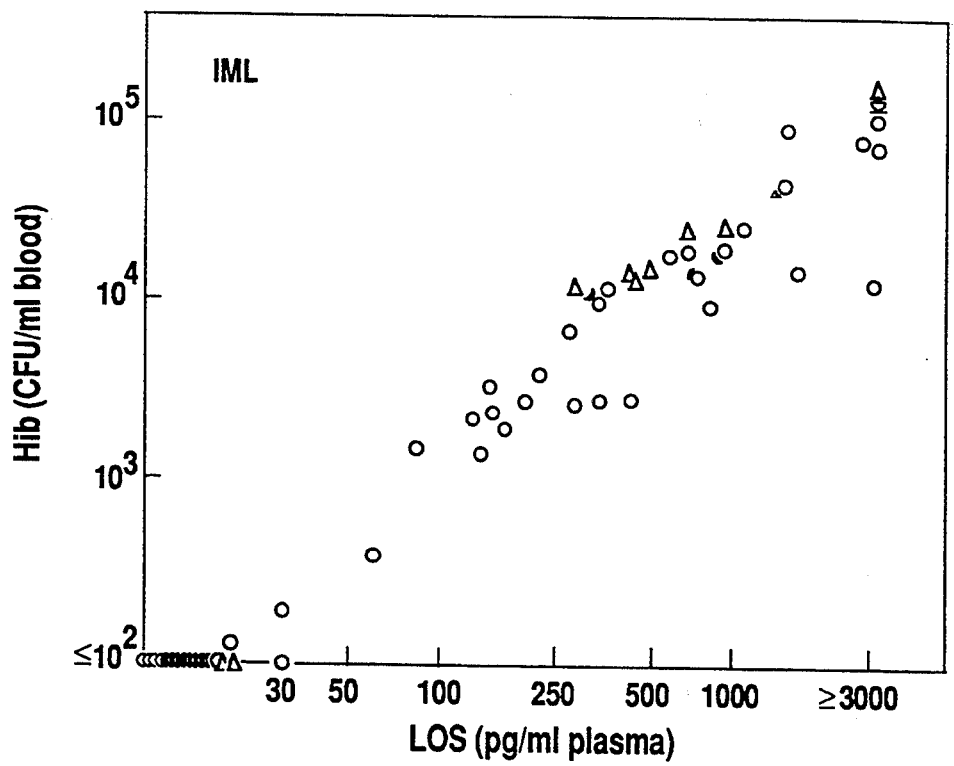
FIG. 3 shows levels of Hib DL42 ( ) and DL301 ( ) bacteremia and concentrations of Hib LOS in infant rat plasma samples as detected by immunolimulus assay (r=0.845, p<0.001). Open symbols represent uninfected animals and are present only on the left side of the x-axis.

Forty-two (98%) of 43 rats with culture-proven Hib DL42 or DL301 bacteremia had detectable concentrations of LOS in their plasma by IML assay. Furthermore, there was a significant correlation (r=0.845, p<0.001) between the LOS concentrations measured and the magnitude of bacteremia in the animals. None of the uninfected rats had detectable LOS in their plasma samples, while one blood culture-negative sample from a rat challenged with Hib DL42 was positive with IML. There were no significant differences between the IML results obtained with the two different Hib strains DL42 and DL301, both of which are reactive with MAb 4C4 (FIG. 3).

Figure 4:
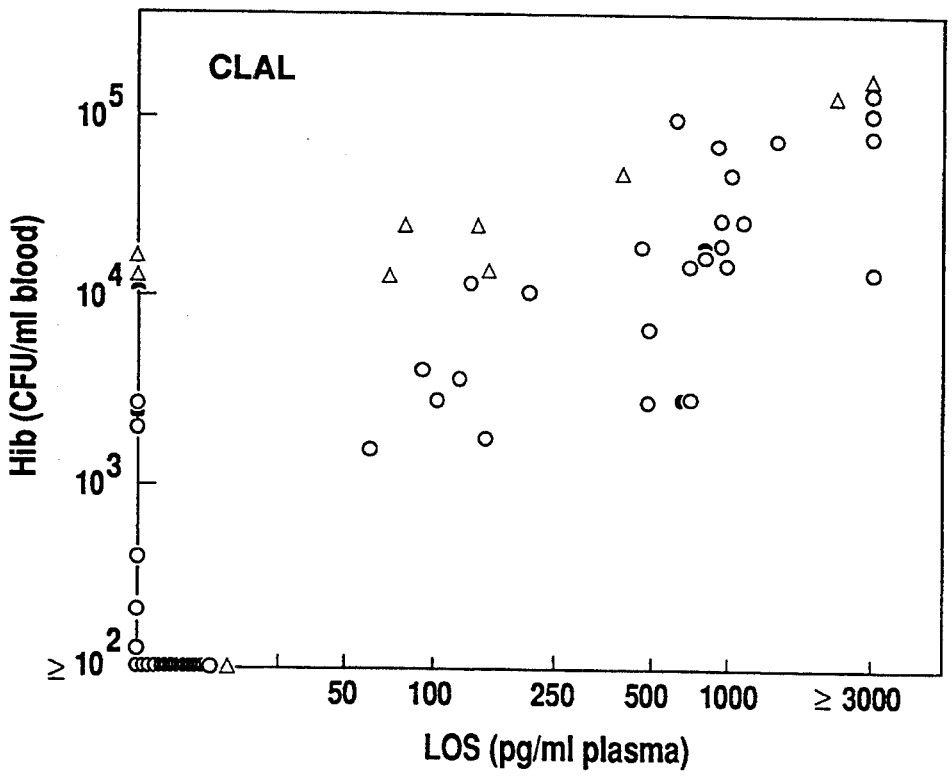
FIG. 4 shows levels of Hib DL42 ( ) and DL301 ( ) bacteremia and concentration of Hib LOS in plasma samples as detected by CLAL assay (r=0.787, p<0.001). Open symbols represent uninfected infant rats and are present only on the left side of the x-axis.

The CLAL assay was positive with 27 (63%) of the Hib-infected rats, and negative with all those that did not have detectable bacteremia (FIG. 4). There was a significant correlation between the endotoxin concentrations measured with the CLAL assay and the levels of bacteremia (r=0.787, p<0.001); the correlation between IML and CLAL results was also significant (r=0.933, p<0.001).

EXAMPLE 4

Immunolimulus Assay for Hib LOS DL26 or *Escherichia coli* in Plasma From Rats Infected with These Bacteria All the rats infected with Hib DL26 (twelve animals) or *Escherichia coli* K1 (twelve animals) had detectable bacteremia and 19 (91%) of them had detectable concentrations of endotoxin when tested by CLAL (Table 2). However, all were negative with the IML assay using MAb 4C4; this particular MAb is not reactive with either of these strains (Table 2). Six of the nine *Escherichia coli* K1-infected rats, which had highest concentrations of bacteria in blood, had nonspecific positive result in the IML assay, reminiscent of the findings involving the effects of very high concentrations of LPS on the IML assay in earlier in vitro experiments (Table 1). When these plasma samples were retested in the IML at 1:10 and 1:100 dilutions, all of these samples yielded negative results in IML assay, thus confirming the specific nature of the assay. The results are presented in Table 2.

TABLE 2

Bacteremia, as detected by blood culture, and endotoxemia, as detected by chromogenic Limulus (CLAL) and by immunolimulus (IML) assays, in infant rats infected with Hib DL26 or *Escherichia coli* K1.

| | Hib DL 26 | | | *Escherichia coli* K1 | | |
|---|---|---|---|---|---|---|
| Rat No. | Bacteremia (cfu/ml) | CLAL (ng/ml) | IML (ng/ml) | Bacteremia (cfu/ml) | CLAL (ng/ml) | IML (ng/ml) |
| 1. | $2.1 \times 10^5$ | 2.78 | <0.03 | $2.8 \times 10^7$ | >100 | <0.03 |
| 2. | $1.9 \times 10^5$ | 3.06 | <0.03 | $2.0 \times 10^7$ | >100 | <0.03 |
| 3. | $1.6 \times 10^5$ | 3.03 | <0.03 | $6.3 \times 10^6$ | >100 | <0.03 |
| 4. | $1.2 \times 10^5$ | 3.48 | <0.03 | $3.5 \times 10^6$ | 50.2 | <0.03 |
| 5. | $2.9 \times 10^4$ | 0.17 | <0.03 | $4.0 \times 10^5$ | 18.0 | <0.03 |
| 6. | $2.1 \times 10^4$ | 0.13 | <0.03 | $2.3 \times 10^5$ | 65.9 | <0.03 |
| 7. | $2.1 \times 10^4$ | 0.36 | <0.03 | $1.7 \times 10^5$ | 3.9 | <0.03 |
| 8. | $1.5 \times 10^4$ | 0.34 | <0.03 | $1.4 \times 10^5$ | 17.4 | <0.03 |
| 9. | $1.5 \times 10^4$ | 0.31 | <0.03 | $1.2 \times 10^5$ | 10.0 | <0.03 |
| 10. | $1.5 \times 10^4$ | 0.26 | <0.03 | ND[a] | ND | ND |
| 11. | $1.4 \times 10^4$ | <0.05 | <0.03 | ND | ND | ND |
| 12. | $9.2 \times 10^3$ | <0.05 | <0.03 | ND | ND | ND |

[a] Three rats died before sampling of blood.

EXAMPLE 5

Immunolimulus Assay for the Detection of *Haemophilus ducreyi*

The immunolimulus assay was applied to the detection of *H. ducreyi*, the causative agent of chancroid. To exemplify the applicability of the immunolimulus assay to the detection of *H. ducreyi*, a study was conducted wherein a monoclonal antibody specific for *H. ducreyi* LOS was employed in an assay essentially as set forth in Example I. The monoclonal antibody to *H. ducreyi* LOS employed in these studies was prepared as follows:

Cell envelopes from *H. ducreyi* strain 35000 were used to immunize female BALB/c mice. A 50–100μg quantity of cell envelope protein suspended in 0.1 ml of Freund's complete adjuvant was injected intraperitoneally into several mice. Approximately four weeks later, two of these mice were given an intravenous injection with 50 μg of these cell envelopes and then the spleens were removed for use in the hybridoma fusion protocol. The hybridoma cell line 3E6 secreting an IgG monoclonal antibody reactive with *H. ducreyi* LOS was identified by screening hybridoma culture supernatants in Western blot analysis against cell envelopes and then against proteinase K-treated cell envelopes. This Mab (3E6) was found to be reactive with every *H. ducreyi* strain tested to date (at least 20 strains) and does not react with *H. influenzae* strains, with *Treponema pallidum*, or with two *Neisseria gonorrhoeae* strains in colony blot-radioimmunoassay analysis.

The immunolimulus assay incorporating *H. ducreyi* LOS-specific antibody 3E6 was applied first to the detection of *H. ducreyi* that had been grown in vitro and resuspended in pyrogen-free PBS. This sample was prepared by growing *H. ducreyi* strain 35000 on chocolate agar plates overnight at 33° C. in a candle extinction jar. The resultant colonies were scraped off the surface of the agar plates and suspended in pyrogen-free PBS to a concentration of 10×8 cfu. After mixing by vigorous vortexing, the cell suspension was diluted to approximately 10×7 cfu per ml in pyrogen-free PBS. This suspension was then heated at 75° C. for 12 minutes. Serial dilutions of this heated cell suspensions were then prepared using pyrogen-free PBS and 50 μl portions of these dilutions were used as test samples in the immunolimulus system with monoclonal antibody 3E6. The limit of detection of *H. ducreyi* in this system was 50 cfu or 10×3 cfu per ml.

A second sample, this one obtained from lesions caused by *H. ducreyi*, was also tested with the foregoing immunolimulus assay. In this study, *H. ducreyi* organisms were grown in vivo in a temperature-dependent rabbit model, as described in U.S. Ser. No. 690,152, filed Apr. 23, 1991, incorporated herein by reference. Briefly, necrotic lesions were developed on the backs of shaved rabbits as follows: Male New Zealand white (NZW) rabbits (2.7 to 3.2 kilograms) were obtained from commercial sources and housed in rooms with temperatures controlled at 15°–17° C. Prior to bacterial inoculation, the dorsal hair of each rabbit was shaved using an animal grooming clipper Model A-5 (Oster Professional Products, Milwaukee, Wis.). Thereafter, the backs of the rabbits were shaved on a daily basis.

*H. ducreyi* strain 35000 used for inoculation into animals were cultivated in candle extinction jars at 33° C. for 14 to 16 hrs. The bacteria were harvested into sterile phosphate-buffered saline (PBS), pH 7.2, using sterile cotton swabs and the cells were washed twice with PBS by repeated centrifugation and resuspension, and cell suspensions containing varying numbers of cfu of *H. ducreyi* were prepared in pyrogen-free saline. The *H. ducreyi* cell suspensions were injected intradermally into the shaved backs of the rabbits at duplicate sites, using an injection volume of 0.1 ml.

Rabbits were housed in a temperature-controlled room at 15°–17° C. to lower their skin temperature. Animals housed at 15°–17° C. had an average surface skin temperature 2° C. lower than that of animals housed at 23°–25° C. After about 2–4 days, lesions were found to develop. Two to five days after intradermal injection, material was aspirated from the resultant lesions and the content of viable *H. ducreyi* organisms in each sample determined. Bacteria were recovered from skin lesions by injecting 0.1 ml of sterile, pyrogen-free PBS into the lesion site with a 25-gauge needle and then aspirating the injected material back into a syringe. The material aspirated from each lesion was brought to a final volume of 1 ml using pyrogen-free PBS. Then, 50 µl aliquots were plated to determine the content of viable *H. ducreyi* in the aspirated material. A 1:5 dilution of this material in pyrogen-free PBS was prepared and heated at 75° C. for 12 minutes. Then, 50 µl samples of both this suspension and further dilutions of this suspension were used in the immunolimulus assay. A positive reaction in this assay was obtained with samples containing as few as 200 cfu of viable *H. Ducreyi* per ml.

The foregoing studies demonstrate the applicability of the immunolimulus assay as a rapid diagnostic test for chancroid.

PROPHETIC EXAMPLE 6

The present example outlines the procedure contemplated by the Applicants to be useful for the successful practice of detecting gram-negative bacterial lipopolysaccharides.

Detection of Gram-Negative Bacteremia, Septicemia, Endotoxemia and Detection of the Presence of Gram-Negative Bacterial Endotoxin in Fluids In this method, a monoclonal antibody or monoclonal antibodies broadly cross-reactive with essentially all LPS or LOS molecules of gram-negative bacteria will be employed as the capture agent. The general protocol to be followed is that described in the preceding examples. The antibody preferred for this particular method would be a mixture of antibodies including but not limited to, XMMEN-OE5, XMMEN-LY1, XMMEN-LY2, and XMMEN-J5D (11). These antibodies would be used to coat microtiter wells, the test fluid would then be subjected to heating at 75° C. for 12 min, and then reacted with the microtiter wells. After extensive washing of the wells, the Limulus lysate detection system would be added to the wells, followed by chromogenic substrate.

PROPHETIC EXAMPLE 7

The present example outlines the procedure contemplated by the inventors to be useful in the detection of *Pseudomonas aeroginosa*.

Detection of *Pseudomonas aeruginosa* and *Pseudomonas maltophilia*

The monoclonal antibody XMMPS-605 (11) would be the appropriate capture agent for a system designed to detect the presence of the LPS of either *Pseudomonas aeruginosa* or *Pseudomonas maltophilia*. This antibody (XMMPS-6-5) could be used alone or in concert with the following monoclonal antibodies: XMMPS-OP1, XMMPS-OP2, XMPPS-OP3, XMMPS-OP4 and XMMPS-OP7. These five additional monoclonal antibodies react with five of the seven Fisher types of *Pseudomonas aeruginosa* (11). In this particular method, the monoclonal antibody or antibodies would be used to coat microtiter plate wells. Then, as described for the examples cited above, these wells would be washed, the Limulus lysate detection system would be added, followed by the chromogenic substrate and color development measured and related to the amount of Pseudomonas LPS present.

The present invention has been described in terms of particular embodiments found or proposed by the present inventors to comprise preferred modes for the practice of the invention. It will be appreciated by those of skill in the art that, in light of the present disclosure, numerous changes and modifications can be made in the particular embodiments exemplified without departing from the intended scope of the invention. For example, other monoclonal or polyclonal antibodies could be used for the specific detection of Hib or other LOS. Fragments or functionally equivalent antibodies selective for endotoxin could be exchanged for the examples given. All such modifications are intended to be included within the scope of the appended claims.

REFERENCES

The literature citations appearing within the text of this application are hereby incorporated by reference to the extent they supplement, explain, provide a background for or teach methodology, techniques and/or compositions employed herein.

1. Bayston, K. F., Cohen, J. J. Med. Microbiol. 31, 73–83 (1990).
2. Morbidity Mortality Weekly Report 39/2, 31–34 (1990).
3. Ellner, J. J. Pediatr. Clin. North Am. 30, 365–371 (1983).
4. Jacobs, R. F., Sowell, M. K., Moss, M. M., Fiser, D. H. Pediatr. Infect. Dis. J. 9, 196–200 (1990).
5. Cybulsky, M. I., Chan, M. K. W., and Movat, H. Z. Lab. Invest. 58/4, 365–378 (1988).
6. Levin, J. and Bang, F. B. Bull. Johns Hopkins Hosp. 115, 265–274 (1964).
7. deJongh-Leuvenink, J., Schellekens, J. and Verhoef, J. Infection and Immunity 58, 421–426 (1990).

8. Young et al., Clin. Res. 30/2 (April, 1982).

9. Dunn, D. L., Bogard, W. C. and Cerra, F. B. Surgery 98, 283–90 (1985).

10. Salles, M. -F., Mandine, E., Zalisz, R., Guenounou, M. and Smets, P. J. Infect. Dis. 159, 641–647 (1989).

11. Young et al., U.S. Pat. No. 4,918,163, Apr. 17, 1990.

12. Connelly, U.S. Pat. No. 4,906,567, Mar. 6, 1990.

13. Erich, T., Schellekens, J., Bouter, A., van Kranen, J., Brouwer, E., and Verhoef J. Immunol. 143, 4053–4060 (1989).

14. Pollack, M., Chia, J. K. S., Koles, N. L., Miller, M., and Guelde, G. J. Infect. Dis. 159, 168–188 (1989).

15. Teng N. N. H., Kaplan, H. S., Hebert, J. M., Moore, C., Douglas, H., Wunderlich, A. and Braude, A.I. Proc. Natl. Acad. Sci. USA 82, 1790–1794 (1985).

16. Kirkland, T. N., Colwell, D. E., Michalek, S. M., McGhee, J. R. and Ziegler, E. J. J. Immunol. 137, 3614–3619 (1986).

17. Gulig, P. A., Patrick, C. C., Hermanstorfer, L., McCracken, G. H., and Hansen, E. J. Infect. Immun. 55, 513–520 (1987).

18. Hansen, E. J., Firsch, C. F., McDade, R. L., Jr., and Johnston, K. H. Infect. Immun. 32, 1084–1092 (1981).

19. Kimura, A., Patrick, C. C., Miller, E. E., Cope, L. D., McCracken, G. H., Jr., and Hansen, E. J. Infect. Immun. 55, 1979–1986 (1987).

20. Mertsola, J., Munford, R. S., Ramilo, O., Saez-Llorens, X., Nustafa, M. M., McCracken, G. H., Jr. and Hansen, E. J. J. Clin. Microbiol., 28, 2700–2706 (1990).

21. Teng, N. N. H., Kaplan, H. S., Hebert, J. M., et al. Proc. Natl. Acad. Sci. USA, 82, 1790–1794 (1985)

We claim:

1. A method for detecting bacterial endotoxin in a sample, comprising the steps of:
   (a) contacting a sample suspected of containing a bacterial endotoxin with at least one antibody which specifically binds said/bacterial endotoxin, the sample being contacted with the antibody under conditions effective to bind the antibody to endotoxin that may be present in the sample;
   (b) washing antibody-bound endotoxin to remove contaminants; and
   (c) detecting endotoxin with an amoebocyte lysate.

2. The method of claim 1, wherein the endotoxin is detected by:
   (a) incubating the washed antibody-bound endotoxin with an amoebocyte lysate to activate a protease system of the lysate;
   (b) adding to the lysate a substrate of the protease system of the lysate; and
   (c) measuring amounts of a product formed from action of said protease system on the added substrate, said product being proportional to a level of bacterial endotoxin in the sample.

3. The method of claim 1, wherein the antibody is bound to a solid surface.

4. The method of claim 1 wherein the antibody is specific for a core glycolipid of bacterial endotoxin.

5. The method of claim 1 wherein the antibody is specific for an epitope comprising a region proximal to bacterial endotoxin lipid A.

6. The method of claim 1 wherein the antibody is specific for an epitope comprising lipid A.

7. The method of claim 1 wherein the antibody is specific for an epitope comprising a heptose and a ketodeoxyoctonate.

8. The method of claim 1 wherein the antibody is a MAb obtained from hybridoma cell line XMMEN-OE5 having ATCC Accession No. HB9081.

9. The method of claim 1 wherein the antibody comprises a binding fragment thereof.

10. The method of claim 1 wherein the bacterial endotoxin is a lipooligosaccharide or lipopolysaccharide of a gram-negative bacterium.

11. The method of claim 1, wherein the bacterial endotoxin is of a gram-negative bacterium of the genus Escherichia, Bordetella, Branhamella, Salmonella, Haemophilus, Klebsiella, Proteus, Enterobacter, Pseudomonas, Pasteurella, Acinetobacter or Neisseria.

12. The method of claim 1 wherein the antibody is specific for an O-antigen.

13. The method of claim 12 wherein the antibody is is specific for the O-antigen of *Salmonella typhi.*

14. The method of claim 1 wherein the amoebocyte lysate is obtained from the blood of *Tachypleus tridentatus, Tachypleus gigas, Carcinoscorpius rotundicauda* or *Limulus polyphemus.*

15. The method of claim 2 wherein the substrate added to the reaction comprises a chromogenic substrate.

16. The method of claim 1 wherein the sample comprises plasma, serum, cerebrospinal fluid or urine.

17. The method of claim 1 wherein the sample is heated prior to contacting with the antibody.

18. The method of claim 17 wherein the sample is heated at a temperature of about 75° C.

19. A method of detecting *Haemophilus influenzae* type b lipooligosaccharide (Hib LOS) in a sample suspected of containing such LOS, comprising the steps of:
   (a) contacting the sample with at least two antibodies specific for Hib LOS to form an immunocomplex between the antibodies and the Hib LOS;
   (b) washing the immunocomplex;
   (c) incubating the washed Hib LOS with Limulus amoebocyte lysate to a protease system in the Limulus lysate; and
   (d) detecting the presence of LOS by detecting a product formed from action of the protease system on a substrate.

20. The method of claim 19, wherein the antibody is specific for lipid A-distal outer core oligosaccharide.

21. The method of claim 19 wherein the antibody is an IgG3 monoclonal antibody specific for an epitope in the oligosaccharide region of Hib LOS DL26 or Hib LOS DL42.

22. A method of detecting *Haemophilus ducreyi* LOS in a sample suspected of containing such LOS, the method comprising the steps of:
   (a) contacting the sample with at least one antibody specific for *Hemophilus ducreyi* LOS to form an immunocomplex between the antibody and LOS that may be present in the sample;
   (b) washing the immunocomplex;
   (c) incubating the washed *H. ducreyi* with Limulus amoebocyte lysate to activate a protease system in the Limulus lysate; and
   (d) detecting the presence of LOS by detecting a product formed from action of the protease system on a substrate.

23. A kit for the detection of bacterial endotoxin in a sample, the kit comprising:

(a) A carrier, compartmentalized to receive at least two containers in confinement therein;

(b) A first container positioned in one of the compartments, the first container comprising at least one solid phase antibody specific for bacterial endotoxin; and (c) A second container positioned in another compartment, the second container comprising an amoebocyte lysate or a chromogenic substrate for detecting release of a protease system by bacterial endotoxin.

24. The kit of claim 23, further defined as including both a container comprising the amoebocyte lysate and one comprising the chromogenic substrate.

25. The kit of claim 23, wherein the antibody comprises a monoclonal antibody.

26. The kit of claim 23, wherein the antibody comprises an antibody that specifically binds an epitope of an oligosaccharide proximal to lipid A or to lipid A within an inner core region of a gram-negative bacterium.

27. The kit of claim 23, wherein the antibody is a monoclonal antibody obtained from hybridoma cell line XMMEN-OE5 having ATCC Accession No. HB9081.

28. The kit of claim 23, wherein the amoebocyte lysate is obtained from blood of *Tachypleus tridentatus, Tachypleus gigas, Carcinoscorpius rotundicauda* or *Limulus polyphemus.*

29. A kit comprising:

(a) A carrier, compartmentalized to receive at least two containers in confinement therein;

(b) A first container positioned in a compartment, the first container comprising two solid phase antibodies specifically binding to epitopes of *Haemophilus influenzae* type b endotoxin in combination with amoebocyte lysate; and (c) A second container positioned in a compartment, the second container comprising an amoebocyte lysate or a chromogenic substrate for detecting protease released from amoebocyte lysate.

30. The kit of claim 29, further defined as enclosing both a container comprising the amoebocyte lysate and one comprising the chromogenic substrate.

31. The kit of claim 29 wherein the antibody is an IgG3 monoclonal antibody specific for an oligosaccharide epitope in Hib LOS DL42 or DL26.

32. The kit of claim 29 wherein the first container comprises MAbs 4C4 and DL42.

33. The kit of claim 29 wherein one or more components are supplied in lyophilized form.

34. A kit comprising:

(a) A carrier, compartmentalized to receive at least two containers in confinement therein;

(b) A first container positioned in a compartment, the first container comprising at least one solid phase antibody specifically binding to epitope of *Haemophilus ducreyi* LOS; and (c) A second container positioned in a compartment, the second container comprising an amoebocyte lysate or a chromogenic substrate for detecting protease released from amoebocyte lysate.

35. The kit of claim 34 further defined as including both a container comprising the amoebocyte lysate and one comprising the chromogenic substrate.

36. The kit of claim 34 wherein one or more components are supplied in lyophilized form.

* * * * *

UNITED STATES PATENT AND TRADEMARK OFFICE
CERTIFICATE OF CORRECTION

PATENT NO. : 5,356,778

DATED : October 18, 1994

INVENTOR(S) : Eric J. Hansen, et al.

It is certified that error appears in the above-indentified patent and that said Letters Patent is hereby corrected as shown below:

In claim 1, column 15, line 41, delete "said/bacterial" and insert --said bacterial-- therefor.

In claim 11, column 16, lines 14-16, delete "Escherichia, Bordetella, Branhamella, Salmonella, Haemophilus, Klebsiella, Proteus, Enterobacter, Pseudomonas, Pasteurella, Acinetobacter" and insert --*Escherichia, Bordetella, Branhamella, Salmonella, Haemophilus, Klebsiella, Proteus, Enterobacter, Pseudomonas, Pasteurella, Acinetobacter*-- therefor.

In claim 11, column 16, line 16, delete "Neisseria" and insert --*Neisseria*-- therefor.

In claim 19, column 16, lines 41 and 42-43, delete "Limulus" and insert --*Limulus*-- therefor.

In claim 20, column 16, line 63, delete "Limulus" and insert --*Limulus*-- therefor.

In claim 32, column 18, line 14, delete "DL42" and insert --12D9-- therefor.

UNITED STATES PATENT AND TRADEMARK OFFICE
CERTIFICATE OF CORRECTION

PATENT NO. : 5,356,778
DATED : October 18, 1994
INVENTOR(S) : Eric J. Hansen, et al.

It is certified that error appears in the above-indentified patent and that said Letters Patent is hereby corrected as shown below:

In claim 29, column 18, line 2, delete "in combination with amoebocyte lysate" therefor.

Signed and Sealed this

Thirteenth Day of December, 1994

Attest:

BRUCE LEHMAN

Attesting Officer

Commissioner of Patents and Trademarks